(12) United States Patent
Hotier et al.

(10) Patent No.: US 7,288,200 B1
(45) Date of Patent: *Oct. 30, 2007

(54) SYSTEM FOR INJECTING A BY-PASS FLUID IN A SEPARATION METHOD IN A SIMULATED MOVING BED

(75) Inventors: Gérard Hotier, Rueil Malmaison (FR); Xavier Decoodt, Montreuil (FR); Gilles Ferschneider, Saint-Symphorien d'Ozon (FR); Jean-Christophe Viguie, Saint-Symphorien d'Ozon (FR)

(73) Assignee: Institut Francais du Petrole, Ruiel Malmaison, Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/762,580

(22) PCT Filed: May 26, 2000

(86) PCT No.: PCT/FR00/01455

§ 371 (c)(1),
(2), (4) Date: Feb. 9, 2001

(87) PCT Pub. No.: WO00/74807

PCT Pub. Date: Dec. 14, 2000

(30) Foreign Application Priority Data

Jun. 9, 1999 (FR) .................................. 99 07309

(51) Int. Cl.
*B01D 15/08* (2006.01)

(52) U.S. Cl. ..................................... 210/659; 210/198.2

(58) Field of Classification Search ................ 210/659, 210/670, 672, 198.2, 269, 284
See application file for complete search history.

(56) References Cited

U.S. PATENT DOCUMENTS 2,985,589 A    5/1961   Broughton ................... 210/676

(Continued)

FOREIGN PATENT DOCUMENTS

EP            769316 A        4/1997

(Continued)

*Primary Examiner*—Ernest G. Therkorn
(74) *Attorney, Agent, or Firm*—Millen, White, Zelano & Branigan, P.C.

(57) ABSTRACT

Device and process for separating at least one compound from a mixture in a simulated moving bed, comprising:
- an enclosure comprising several absorbent beds, two adsorbent beds being separated by a fluid distribution and extraction plate (Pi), the plate comprising one or more distribution, mixing and/or extracting panels, comprising a chamber (Ci),
- main fluid delivery (4) and extraction (2) lines,
- several secondary fluid extraction or injection lines (10, 11, 12, 13, Ti),
- a bypass circuit communicating a distribution plate with a bypass line,
- means (14, Voi,j, 20) communicating at least one chamber (Ci) with at least one bypass line (Li,j),
- at least one of the ends of a bypass line communicates with a zone Ri, R'I of an adsorbent bed, said zone being distinct from a distribution chamber (Ci) and another end is connected to said chamber (Ci).

24 Claims, 7 Drawing Sheets

U.S. PATENT DOCUMENTS

| | | | | |
|---|---|---|---|---|
| 3,268,605 A | | 8/1966 | Boyd | 585/821 |
| 3,592,612 A | | 7/1971 | Ballard | 422/191 |
| 4,194,892 A | * | 3/1980 | Jones et al. | 95/95 |
| 4,378,292 A | * | 3/1983 | Haase | 210/266 |
| 4,614,204 A | | 9/1986 | Dolejs | 137/625.11 |
| 5,755,960 A | * | 5/1998 | Callebert et al. | 210/198.2 |
| 5,972,224 A | * | 10/1999 | Hotier et al. | 210/659 |
| 6,146,537 A | * | 11/2000 | Ferschneider et al. | 210/659 |
| 6,156,197 A | * | 12/2000 | Dessapt et al. | 210/198.2 |
| 6,797,175 B2 | * | 9/2004 | Hotier | 210/659 |

FOREIGN PATENT DOCUMENTS

| | | | |
|---|---|---|---|
| FR | 2772634 | * | 6/1999 |
| FR | 2772634 A | | 6/1999 |
| WO | WO 9503867 A | | 2/1995 |

* cited by examiner

SYSTEM FOR INJECTING A BY-PASS FLUID IN A SEPARATION METHOD IN A SIMULATED MOVING BED

REFERENCE TO RELATED APPLICATIONS

This application is a 371 of PCT/FR00/01455 filed May 26, 2000.

FIELD OF THE INVENTION

The present invention relates to a device for injecting a fluid stream used as a diverted fluid in a separation process using several adsorbent beds, a main fluid stream and several secondary fluids, the beds being separated by at least one fluid distribution plate, the plate can comprise one or more distributor mixer extractor panels allowing to inject and/or to mix and/or to extract one or more secondary fluids by means of a single distribution chamber.

The invention notably applies to the device and to the process described in the claimant's patent application FR-2,772,634 when injection and extraction of secondary fluids are performed by means of a single distribution network commonly referred to as distribution <<spider>>.

The invention also relates to all the processes where it is desired to improve the purity of at least one constituent in a mixture circulating through a solid adsorbent or a solid catalyst.

It can also apply to processes for separating at least one constituent in a mixture wherein any chromatographic adsorption or ion exchange separation is performed for example.

In the description hereafter, the expression <<main fluid>> refers to a fluid stream circulating through the adsorbent beds and the expression <<secondary fluid(s)>> refers to fluids that are used in the separation process, for example the desorbent, the feed, the extract or the raffinate, and which communicate with the outside.

The invention is particularly suited for separation of paraxylene from aromatic hydrocarbon-containing feeds with eight carbon atoms.

BACKGROUND OF THE INVENTION

The prior art describes various devices and processes allowing separation of feeds in a simulated moving bed. U.S. Pat. No. 2,985,589; U.S. Pat. No. 3,214,247; U.S. Pat. No. 3,268,605; U.S. Pat. No. 3,592,612; U.S. Pat. No. 4,614,204; U.S. Pat. No. 4,378,292; U.S. Pat. No. 5,200,075; U.S. Pat. No. 5,316,821 and patent applications EP-0,769,316; FR-2,772,634 and WO-95/03,867 can be mentioned.

In general, a simulated moving bed comprises at least three chromatographic zones, advantageously four or five, each zone consisting of at least one bed or column section.

Between two zones, there is either an injection point for a feed to be fractionated or an injection point for an eluent or desorbent, or a point allowing to draw off an extract between the eluent injection point and the feed injection point situated downstream (in relation to the direction of circulation of the eluent), or a raffinate draw-off point between each mixture injection point and the eluent injection point situated downstream in relation to the direction of circulation of the eluent.

All the beds or column sections form a closed loop comprising at least one flow-controlled pump allowing to recycle the main fluid, for example between the first and the last section.

During the separation process, the injection and draw-off points are generally offset in the same direction (downstream or upstream, still in relation to the direction of circulation of the main fluid) by at least one section or column. This is the basis of the principle of simulated moving bed operation.

During this process, it is important that distribution of the fluid on each adsorbent bed is performed as uniformly and homogeneously as possible.

Distribution on each bed requires collection of the stream coming from the previous bed (main fluid circulating in the direction of the principal axis of the column), the possibility of injecting an auxiliary fluid or secondary fluid therein while mixing these two fluids as thoroughly as possible, or the possibility of drawing off part of the fluid collected, of extracting it in order to send it out of the device and of redistributing a fluid onto the next bed.

The whole of the main fluid or stream can therefore either transit through the adsorber according to the pattern described in U.S. Pat. No. 2,985,589, or a great part or all of this stream can flow out to the outside according to a process described in U.S. Pat. No. 5,200,075.

Another solution consists, as described in patent application FR-2,772,634, in transiting the major part of the main fluid towards the inside and a minor part of this stream towards the outside, typically 2 to 20% of this stream. An advantage of such a system is that the secondary fluid injection and extraction circuits permanently have substantially the same composition. Two distribution plates are connected by an external circuit commonly known as synchronous bypass circuit. The function of this circuit is notably to circulate the minor part of the stream drawn off thus providing an identical composition. The secondary fluid extraction on-off valves and a nonreturn valve are connected to the bypass circuit. The circuit can optionally be equipped with an on-off valve or with a control valve allowing to perform injections and extractions on a single plate.

Continuous flushing of the distribution spiders of the distribution plates of the simulated moving bed separation units can be performed in two ways:

1) when each plate is equipped with at least two independent distribution networks ($D_1$ and $D_2$), network $D_1$ of plate P is for example communicated with network $D_2$ of plate P+1, and network $D_1$ of plate P+1 is communicated with network $D_2$ of plate P+2, so as to have a permanent fluid circulation in all the distribution networks on each distribution plate, and, for each plate, a diverted fluid stream flows from a distribution network to the main fluid and a second diverted fluid stream, substantially similar, flows from the main fluid to the second distribution network. The driving force of these flows is provided by the pressure drop caused by the main fluid flowing in the porous granular medium located between two successive distribution plates;

2) when each distribution plate is equipped with only one distribution network, the bypass circuits can be provided only every second bed, for example from plate P to plate P+1, then from plate P+2 to plate P+3. In fact, if a bypass line connected plates P+1 and P+2, a circulation parallel to the adsorber from the top bed to the bottom bed would be obtained. The drawback of establishing a bypass circuit every second bed only is that the internal flow rates would vary from one bed to the other: the beds comprising a bypass circuit would have a flow rate D whereas the beds without a bypass circuit would have a flow rate D+b.

SUMMARY OF THE INVENTION

The present invention relates to a device and to a process that are particularly well-suited for separation devices where the plates are equipped with a single secondary fluid distribution network, the distributor-mixer-extractor panels comprising a single distribution, extraction and/or mixing chamber.

As users' quality requirements have evolved, the purity standard to be reached has changed from values contained in the (99.5; 99.6%) range to a value of 99.8%. Operators must therefore make changes in existing separation units in order to reach these new objectives.

The invention can thus apply to existing units and to new units. It is notably used in adsorption separation processes and devices using countercurrent simulated moving beds and possibly in plants comprising a rotary valve. It finds applications for example in a device comprising a central distribution as described for example in U.S. Pat. No. 4,378,292 where the distribution plates are equipped with only one distribution spider, during revamping of the unit or in case of a significant change in the composition of the feed leading to a change in the configuration of the unit. The invention also applies for debottlenecking of a unit.

More generally, the change introduced according to the invention is particularly well-suited in the following cases:

in case of a change in the composition of the feed connected with the layout of the complex, it is for example possible to change the isomerization type so as to coproduce benzene or, on the contrary, to decide to stop coproduction of benzene in order to produce more paraxylene. The ethylbenzene content of the feed to be processed can thus change from 2% to 15% and its paraxylene content can change from 23% to 17%.

In case of debottlenecking operations in a unit in order to replace the molecular sieve and/or to mechanically reinforce the distribution plates. When this type of modification is required, it involves changing the existing rotary valve. A configuration change requires replacement of the rotor of the valve, a capacity increase requires doubling of the rotary valve by installing a second valve in parallel. These changes are very expensive and can be advantageously replaced by suppressing the rotary valve and by replacing it by 96 on-off valves whose total cost is only about half as expensive.

The invention relates to a device allowing to separate at least one compound from a mixture or from a body by adsorption, with a simulated moving bed, comprising at least:

an enclosure or column comprising one or more adsorbent beds (Ai), two adsorbent beds being separated by at least one fluid distribution and extraction plate (Pi), the plate comprising one or more panels allowing to distribute, mix and/or extract fluids, at least one main fluid delivery line and one main fluid extraction line, several secondary fluid extraction or injection lines, a bypass circuit communicating a distribution plate with at least one bypass line (Li,j), the panel comprises only one distribution, mixing and/or extraction chamber (Ci).

It is characterized in that:

the device comprises means for communicating at least one chamber (Ci) with at least one bypass line (Li,j), at least one end of a bypass line communicates with a zone Ri, R'i of an adsorbent bed, said zone being distinct from a distribution chamber (Ci), and another end is connected to said chamber (Ci).

The communication means comprise, for example, at least one valve Voi,j arranged on at least one bypass line (Li,j), and the end of the bypass line that is not connected to the zone of the adsorbent bed can be connected to a delivery and/or extraction line (Ti).

The communication means comprise for example at least one rotary valve, said rotary valve being connected to at least one delivery and/or extraction line (Ti) and to at least one bypass line (Li,j), said valve comprising means allowing at least to communicate a delivery and/or extraction line with at least one bypass line.

The rotary valve allows for example to communicate several groups of lines, group $G_1$, group $G_2$ and group $G_3$, said valve comprising:

a stator provided with several means (E, F, R, S) for circulating the fluid(s) of group $G_1$, means allowing passage of at least two fluids $F_1$, $F_2$ belonging to group $G_3$, a rotor equipped with means allowing passage of fluids of group $G_3$ and means allowing communication of either the fluids of group $G_1$ with group $G_3$ or of group $G_3$ with group $G_3$, the number of means allowing passage of fluid $F_1$ is substantially the same as the number of means allowing passage of fluid $F_2$, said valve comprises means for communicating at least two fluids of group $G_3$ and section of flow $S_1$ of the ports for fluid $F_1$ is different from section of flow $S_2$ of the ports intended for fluid $F_2$.

The passage means of the valve intended for fluid $F_1$ and for fluid $F_2$ have for example flow surface areas $S_1$ and $S_2$ respectively, and the $S_1/S_2$ ratio is about 4 and preferably ranges between 2 and 10.

The means for communicating the fluids of group $G_3$ can consist of slots arranged in a layer of material or liner deposited on the lower face of the rotor.

A slot has for example a depth <<pe>> and the value of the depth is at least equal to the thickness <<e>> of the liner.

Circulation means (E, R, S, F) arranged on the valve consist for example of several grooves arranged on the resting face or upper face of the stator and the slots are arranged in the liner.

The number of these circulation means is for example 4.

The column can comprise a non-perforated central tube over at least part of the length thereof, and the panels forming a plate can exhibit a tangential type cutout, the zone Ri, R'i where the diverted fluid is reinjected comprises at least one means intended for distribution of the diverted fluid, the end of the bypass line opening into said means, and said means comprise an annular ring mounted on the central tube.

The fluid distribution circuit is for example arranged around said enclosure, and it can comprise a main line divided into several secondary lines so that the fluid(s) reach the panels forming a plate substantially at the same time.

The plates can exhibit a parallel type cutout and the fluid distribution device can comprise a main line, the bypass line is for example connected to an adsorbent bed by means of a device comprising transfer ports, said device being mounted on the fluid distribution spider.

A plate is for example delimited by a lower grid and an upper grid, and the end of the bypass line connected to the adsorbent bed is connected to a distribution means arranged above said upper grid.

A plate can consist of several panels exhibiting a radial type cutout, the enclosure comprises a central tube and a secondary fluid distribution ring associated with a distribution plate, diverted fluid distribution means, said means being arranged below the distribution ring and said means being connected to the end of the bypass line, itself connected to a zone of an adsorbent bed.

The diverted fluid distribution means comprise for example at least one diverted fluid distribution ring, said ring being arranged within a perforated means (such as a grid), said means having a substantially conical shape.

The perforated means comprises for example a wall forming an angle $\alpha$ with the central tube and said ring is placed at a distance a from said grid.

According to an embodiment, the column comprises a substantially central mast comprising one or more mast elements, including at least:
- an upper part,
- a distributor-collector part comprising one or more secondary ports and at least one main port, the sections of flow of the secondary ports and of the main port being different,
- a lower part,
- the distributor-collector part(s) are arranged between the upper part and the lower part,
- a sealing element arranged between the distributor-collector part and the lower part,
- a separation element arranged on the distributor-collector part, thus delimiting two fluid circulation spaces.

The invention also relates to a process for injecting a diverted fluid in a simulated moving bed separation process comprising at least the following stages:
- circulating a main fluid through several adsorbent beds,
- injecting and extracting secondary fluids (feed, desorbent, . . . ) according to a suitable sequence to achieve separation of the constituents to be separated from the feed,
- injecting a diverted fluid.

It is characterized in that at least part of the main fluid is circulated outside the enclosure allowing separation by means of a bypass line comprising at least two ends, one end being connected to a zone of an adsorbent bed distinct from a chamber (Ci) so as to inject and/or to draw off part of the main fluid in the zone.

A fraction of the main fluid is for example drawn off from a chamber (Ci) corresponding to a plate Pi and this main fluid fraction is injected into a zone of adsorbent bed Ai+1.

At least a fraction of the main fluid can be drawn off from a zone of an adsorbent bed Ai and said fraction is injected into chamber Ci.

The device and the process are for example suited for separation of paraxylene from aromatic hydrocarbon-containing feeds with eight carbon atoms.

BRIEF DESCRIPTION OF THE DRAWINGS

Other features and advantages of the invention will be clear from reading the description hereafter of several embodiments of the device and of the associated process, given by way of non limitative example, with reference to the accompanying drawings wherein:

FIGS. 2A and 2B show two variants using <<rotary>> type valves, FIG. 3 gives an example of a diverted fluid injection device arranged above a distribution plate, FIG. 4 diagrammatically shows a specific application of the invention to a separation column comprising a central girder or tube.

DETAILED DESCRIPTION

Figure 1:
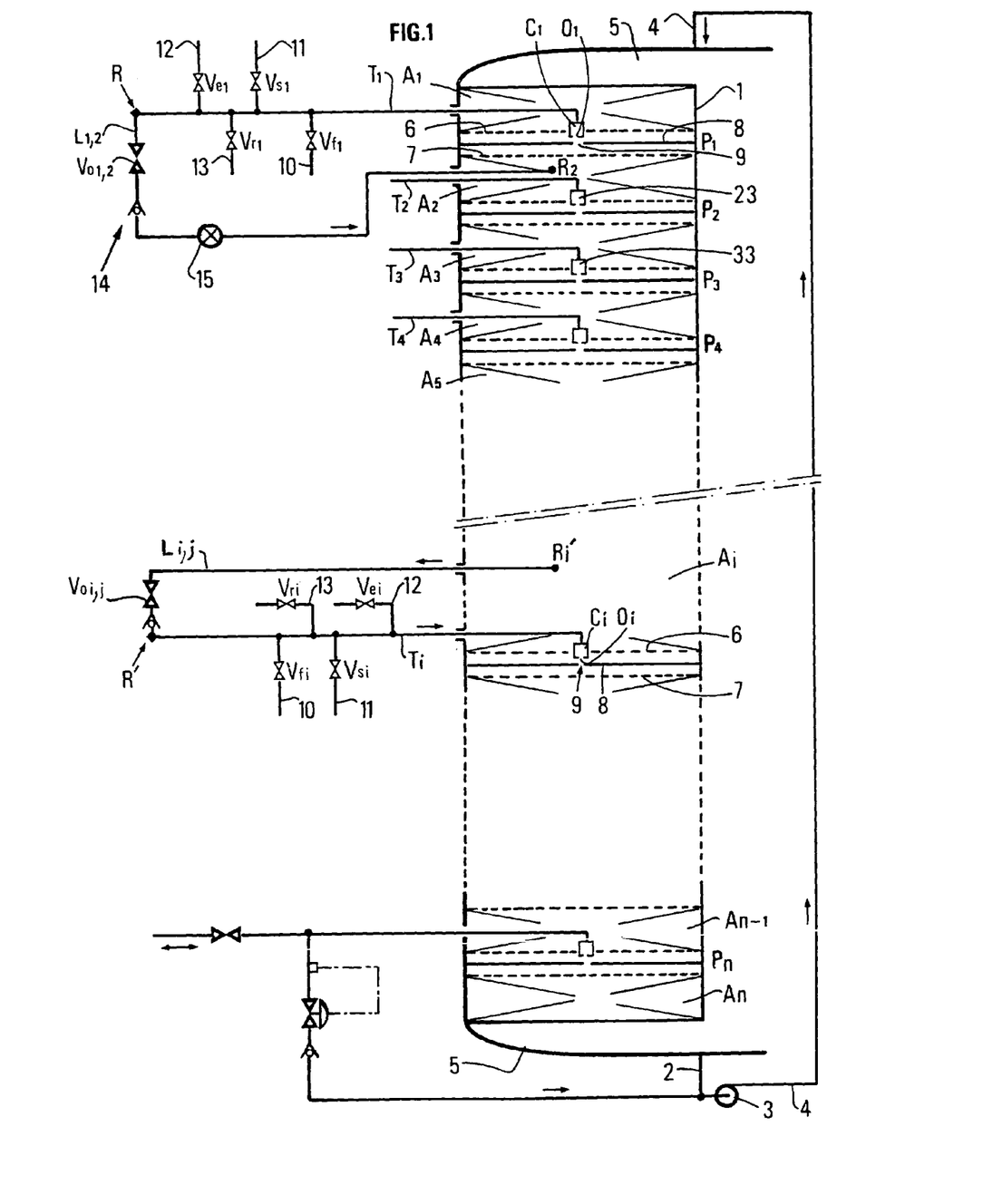
FIG. 1 shows two variants for arranging bypass lines in relation to a separation column.

FIG. 1 shows a simulated moving bed chromatographic separation column equipped with several bypass lines Li,j. For simplification reasons, this figure diagrammatically shows two procedures for connecting a bypass line to an adsorbent bed and to a distribution-mixing-extraction chamber. This connection is achieved according to the invention between a distributor plate Pi and a zone of an adsorbent bed arranged upstream or downstream from the plate. The plate and the zone of the adsorbent bed where the diverted fluid is injected can have the same suffix or different suffixes.

The column comprises an enclosure 1, for example substantially cylindrical, which is filled with an adsorbent distributed among several beds $A_1$ to $A_n$, at least one fluid distribution plate Pi being arranged between two adsorbent beds. A plate Pi comprises one or more panels or distribution-mixing-extraction panels whose function is to distribute, to extract and/or to mix one or more fluids, each panel comprising a distribution-extraction-mixing chamber Ci connected to the outside via a fluid distribution spider.

A plate Pi notably comprises an upper grid 6 supporting the adsorbent bed, a distribution, extraction and/or mixing chamber Ci, a lower grid 7, means such as a baffle 8 allowing to separate lower grid 7 from upper grid 6. Baffle 8 is provided with a central opening 9 allowing circulation of the fluids. Chamber Ci comprises for example in its lower part one or more ports Oi. These ports Oi allow passage of the secondary fluid. The latter is either fed into the next bed after being mixed with the main fluid that has flowed through the main bed, or drawn off through the corresponding transfer line.

Various configuration can be considered for the distribution-mixing-extraction panels, notably geometries where the panel comprises a single distribution, extraction and/or mixing chamber for one or more fluids.

The main fluid circulates in the direction of the longitudinal axis or principal axis of the column. It is extracted through a line 2, recycled by means of a pump 3 and a line 4 to the top of the column. The column can be arranged with a substantially vertical or substantially horizontal axis. The main fluid flows inside the column with a piston type flow or a plug flow, the composition and the flow front being substantially uniform at any point of the column section. A fluid distribution device (not shown in the figure) connected to line 4 can possibly be provided at the top of the column.

A distribution, extraction and/or mixing chamber Ci is connected to the outside of the column by means of a circuit comprising a line Ti connected to several secondary fluid transfer lines. These lines comprise for example a feed injection line 10, a desorbent injection line 11, an extract draw-off line 12 and a raffinate draw-off line 13. Each transfer line is equipped with valves Vfi, Vei, Vsi and Vri where suffix i corresponds to plate Pi and f designates the feed, e the extract, s the desorbent and r the raffinate. All these valves are connected to sequential permutation means suited to periodically move each secondary fluid injection point or secondary fluid draw-off point forward by one bed in the direction of circulation of the main fluid, i.e. downwards, so as to obtain simulated moving countercurrent operation. On the other hand, if simulated cocurrent operation is desired, opening of the valves will be permuted upwards in the opposite direction to the direction of circulation of the fluid.

The column is provided in this example with a bypass line Li,j arranged for example between two plates Pi and Pj, and the two plates can be consecutive.

The working principle of these lines is for example given in patent application FR-2,772,634 whose broad lines are reminded in the present application. A bypass line Li,j is provided with at least one of the devices mentioned hereafter, alone or in combination, i.e. a nonreturn valve 14, a flowmeter 15, a control valve Voi,j, pilot-operated or not by the flowmeter. A pump possibly arranged on the bypass line can possibly compensate for a deficiency of pressure drop.

The bypass circuit is equipped with a valve Voi,j, where suffix o corresponds to the diversion function and suffixes i,j to the plates between which the diverted fluid circulates.

The terms <<upstream>> and <<downstream>> are defined according to the direction of flow of the main fluid in the column.

FIRST EMBODIMENT VARIANT

In the variant shown in the upper part of FIG. 1, a first end of line $L_{1,2}$ intended for diversion of the fluid between plate $P_1$ and plate $P_2$ is connected by a connection point R to fluid delivery and/or extraction line $T_1$ which communicates with chamber $C_1$ and the second end of line $L_{1,2}$ is connected by suitable means, some examples of which are given hereafter, to a zone $R_2$ of the next adsorbent bed $A_2$. Such a layout allows to draw off a fraction of the main fluid from bed $A_1$ situated downstream from plate $P_1$, to extract it through line $T_1$ and to reinject it into adsorbent bed $A_2$ via bypass line $L_{1,2}$ in zone $R_2$. The function of the fraction drawn off is to flush the bypass line and the distribution spider of the plate of bed $A_1$ located immediately downstream.

A sequence cycle of the separation process implemented according to the first embodiment variant can comprise the following stages for example:

1) injection of the feed into chamber Ci, 2) diversion of the fluid between Ci and Ri+1, 3) drawing off the extract from chamber Ci, 4) diversion of the fluid between Ci and Ri+1, 5) injection of the desorbent into chamber Ci, 6) diversion of the fluid between Ci and Ri+1, 7) drawing off the raffinate from chamber Ci, 8) diversion of the fluid between Ci and Ri+1.

The cycle described above can of course start with another stage than the feed injection stage without departing from the scope of the invention.

SECOND EMBODIMENT VARIANT

In the variant shown in the lower part of FIG. 1, a first end of bypass line Li,j is connected to an adsorbent bed Ai, for example in a zone R'i, by suitable means, and the second end of this line is connected by a point R' to secondary fluid delivery and extraction line Ti. This variant allows to draw off, from the adsorbent bed, part of the main fluid in order to reinject it into a distribution chamber of the plate situated downstream from the draw-off point.

Figure 2A:
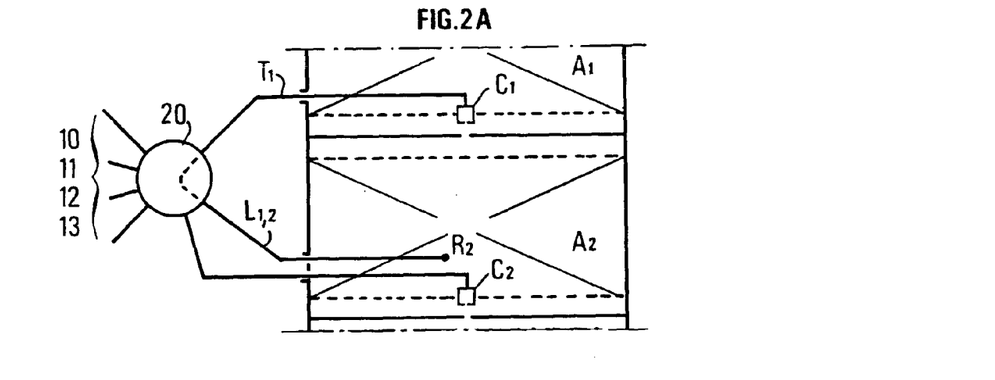
Figure 2B:
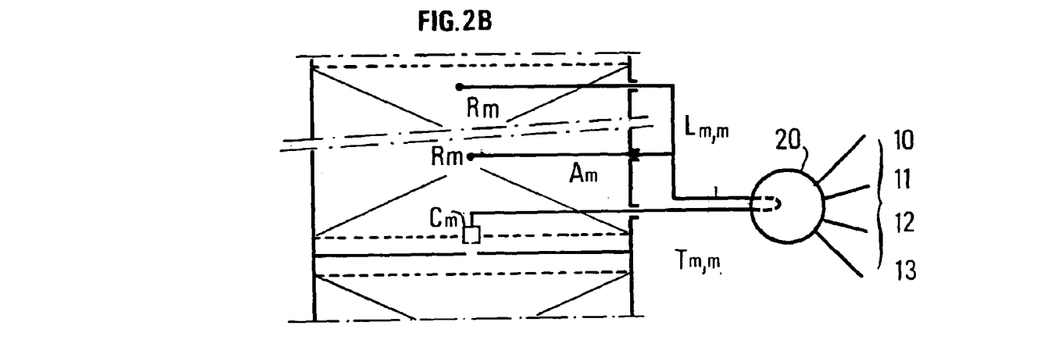

FIGS. 2A and 2B diagrammatically show another variant which differs from FIG. 1 in the secondary fluid delivery and extraction circuit.

For these two variants, the circuit comprises a rotary valve 20 whose function is to communicate the various distribution, extraction and draw-off chambers Ci with fluid sources or lines situated outside the column and also to fulfil the fluid diversion function.

Four secondary fluid transfer lines (10, 11, 12, 13) similar to those shown in FIG. 1 are connected to rotary valve 20.

Valve 20 comprises several transfer lines Ti connected to a chamber Ci, and several bypass line Li,j communicating with a zone of an adsorbent bed Ai.

Rotary valve 20 is provided with inner means allowing to communicate:
- either secondary fluid transfer lines 10, 11, 12, 13 with transfer lines Ti,
- or a zone $R_1$ of an adsorbent bed $A_1$ with an injection, extraction and mixing chamber $C_{i+1}$ to fulfil the fluid diversion function,
- or possibly transfer lines 10, 11, 12, 13 with bypass lines Li,j and transfer lines Ti to fulfil the fluid deviation or diversion function, and simultaneously injection or extraction.

For example, in FIG. 2A, to obtain the fluid deviation or diversion function, the fluid drawn off from chamber $C_1$ circulates in line $T_1$, then, via suitable means located in the valves and described hereafter, it is sent to bypass line $L_{1,2}$ in zone $R_2$ arranged in adsorbent bed $A_2$.

FIG. 2B shows the case where a fluid fraction drawn off from an adsorbent bed Am at a point Rm circulates through bypass line Lm,m, then through transfer line Tm,m via rotary valve 20 prior to being fed into chamber Cm.

The working principle of the separation process is similar to the principle given in the example of FIG. 1.

Figure 3:
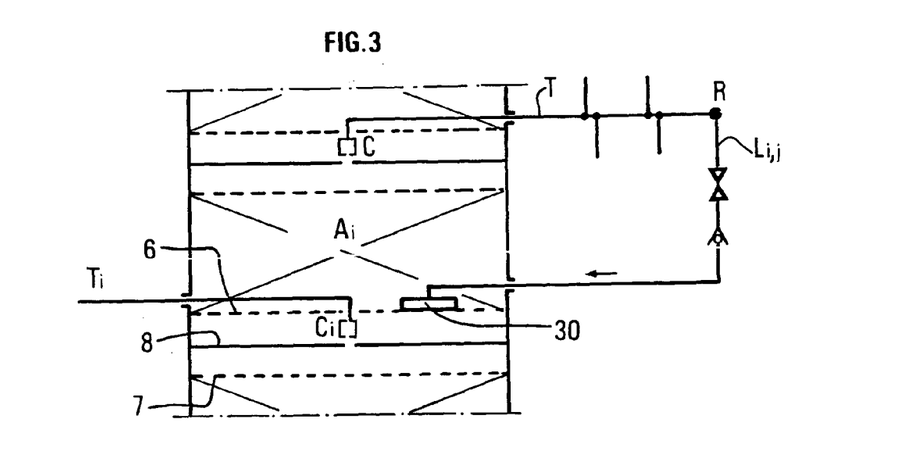

If the end of bypass line Li,j intended for reinjection of a fraction of the main fluid into the bed is connected to an adsorbent bed zone according to a layout given in the upper part of FIG. 1, the reinjection means can consist of a box 30 simply arranged above upper grid 6 of a plate Pi, thus allowing passage of the fraction of the main fluid drawn off (FIG. 3). The dimensions of this box, its surface area for example, are so selected that the fluid stream per unit of surface area is met.

Figure 4:
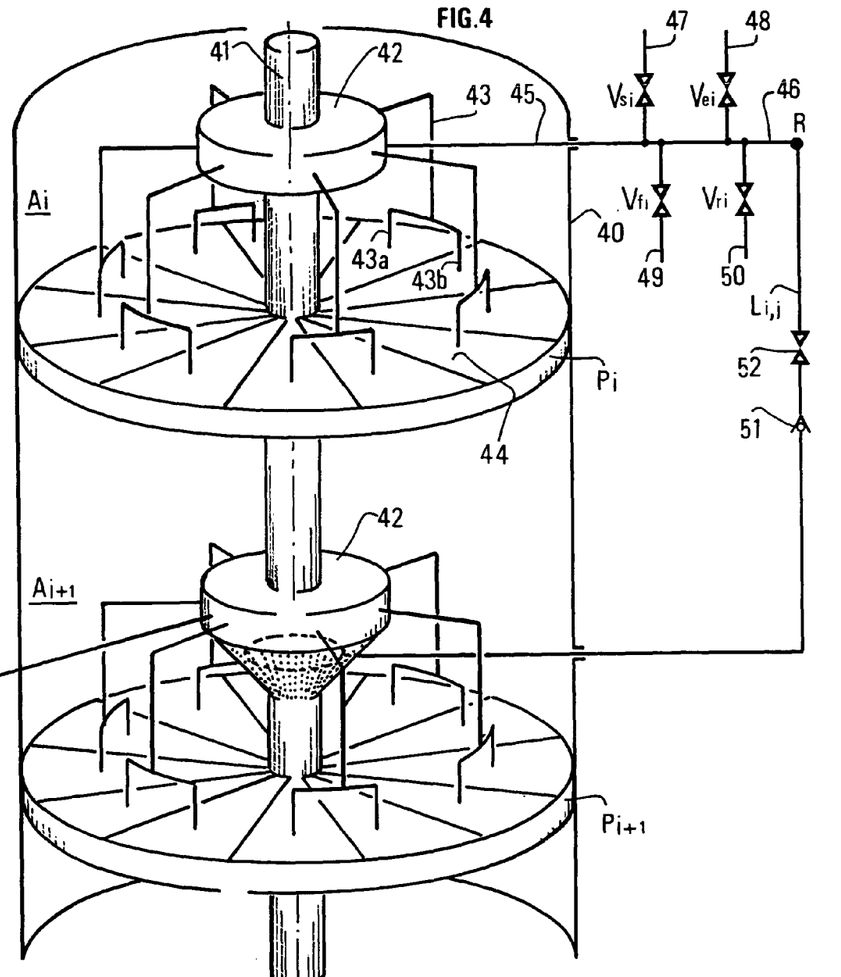

FIG. 4 shows an embodiment variant suited to the case where the separation column comprises an enclosure 40 including a non-perforated central tube 41 for example lined up substantially along the principal axis of the enclosure. The fluid distribution system consists of one ring 42 per bed mounted on non-perforated tube 41. Several pipes 43 or fluid distribution lines extend between a distribution plate Pi and the associated fluid distribution ring so as to connect the various panels 44 of this plate Pi with the outside. In the case of FIG. 4, each line 43 coming from distribution ring 42 is subdivided into two secondary lines 43a and 43b which each reach a panel 44 and the corresponding distribution, mixing, extraction chambers. A transfer line 45 extending between the distribution ring and the outside of the column allows communication with the outside and delivery or extraction of fluids.

According to a variant, the number of lines 43 can be equal to the number of panels 44.

In this embodiment, panels 44 exhibit a radial cutout, i.e. they are separated by radial walls.

Plates Pi are arranged in the enclosure and held up therein by suitable means known to the man skilled in the art. They can be set on girders provided on the central tube and possibly the inner walls of the column.

Line 45 is connected to a line 46 on which the transfer lines and the valves respectively connected to desorbent 47, Vsi, extract 48, Vei, feed 49, Vfi and raffinate 50, Vri, are arranged according to a tee connection for example.

If the column is equipped with one or more bypass lines Li,j, the latter communicating two plates Pi and Pi+1 for example, line Li,j, with j=i+1, is connected to line 46 at a point R and it is equipped for example with a non-return valve 51 and a valve 52.

Valve 52 is open during all the periods of the cycle, except for 2 particular periods:

the period during which desorbent is injected onto plate $P_1$ situated downstream from bed $A_2$, and the period during which feed is injected onto bed $A_2$.

The feed and the desorbent are thus injected on only one bed at a time. Non-return valve 51 closes when extract or raffinate is drawn off at the outlet of bed $A_1$, assuming that the distribution pressure drop through a panel 44, a line 43 and line 45 is higher than the pressure drop through bed $A_2$. Bypass line Li,j, which runs through enclosure 40 and ends below distribution ring 42 for distribution of the diverted stream is located downstream from non-return valve 51.

The zone of the adsorbent bed located below annular distribution ring 42, for which it may be difficult to obtain proper loading of the molecular sieve, is advantageously used for reinjection of the diverted fluid. This zone has a flow area that is greatly disturbed in the absence of diverted fluid during operation of the unit.

Figure 5:
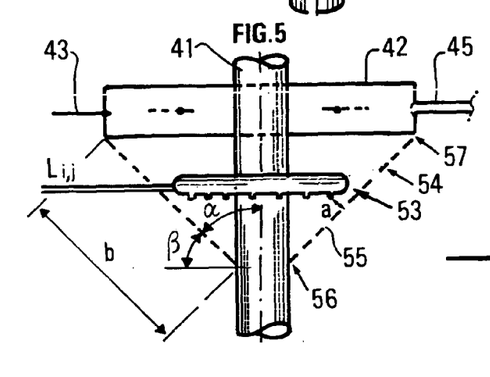
FIGS. 5 and 6 show a detail of the diverted fluid reinjection device and a bottom view of FIG. 4, FIGS. 7A, 7B, 7C show plates with panels exhibiting a tangential cutout, FIGS. 8, 9 and 10 diagrammatically show various possibilities for the diverted fluid distribution devices.
Figure 6:
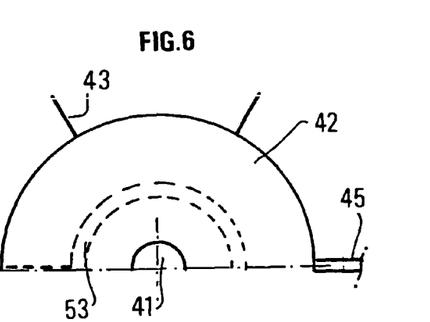

The idea of the variant shown in FIGS. 4, 5 and 6 thus consists in using this non-loaded or non-homogeneously loaded zone to connect the end of the bypass line used for reinjection of the main fluid fraction drawn off from a chamber Ci or the end of the line that will be used to draw off part of the main fluid in order to reinject it into a distribution chamber Ci situated downstream, according to layouts substantially similar to those described in FIG. 1.

The zone can be advantageously equipped with a diverted fluid reinjection device or means whose geometry and characteristics are selected according to the zone.

FIGS. 5 and 6 respectively show a cross-sectional view and a top view of an embodiment of such a fluid reinjection means and its layout in relation to the bulky elements arranged in the column, such as the annular ring and the various lines.

FIG. 5 shows the specific layout of an annular chamber of substantially conical shape, arranged below the distribution ring and whose function is notably to distribute the diverted fluid in the adsorbent bed.

This conical annular chamber is for example mounted on non-perforated central tube 41. The non-perforated central tube comprises for example holding means such as a collar on which the distribution panels rest.

Bypass line Li,j opens for example into a distribution ring 53 (FIG. 5) made from a perforated tube. This ring 53 is for example arranged within the annular distribution chamber delimited by a Johnson or Nagaoka type grid 54 allowing to protect the end of line Li,j and distribution ring 53 from the adsorbent particles. This grid 54 can be welded on the one hand to the lower periphery of the annular distribution ring and, on the other hand, to the non-perforated central tube.

Grid 54 has a wall 55 of substantially conical shape that rests for example, at its lower end 56, on non-perforated central tube 41 and, at its upper end 57, below the annular fluid distribution ring.

The geometry of the annular reinjection chamber is for example defined by the following parameters:

$\alpha$=angle formed by wall 55 and the axis of the central tube, angle $\beta$ complementary to angle $\alpha$ can also be considered, b=length of wall 55, a distance contained between lower end 56 and upper end 57, a=distance at which reinjection ring 53 is positioned in relation to conical wall 55.

The value of angle $\alpha$ corresponds for example to the angle of repose formed by the <<badly loaded>> sieve and the principal axis of the column.

The values of parameters a, b and $\alpha$ are notably selected to obtain:

⇨ the easiest assembly possible,

⇨ a velocity field as homogeneous as possible in the zone of the bed located below the annular reinjection box, ⇨ the most homogeneous distribution possible for the fluid flowing through the annular reinjection box.

The distance c between a plate Pi and the lower connection point situated between the grid and the central tube is selected to allow easy assembly of the panels forming a plate on the support collar.

When using this reinjection means, the fluid flow circulating in the bypass line allows on the one hand to continuously flush the whole of the distribution spider of the upper bed, the transfer line of the inner bed and the transfer and bypass lines, and on the other hand to provide permanent renewal of the fluid of the annular reinjection box.

Furthermore, the diverted fluid passes into a zone of the bed where the flow would be disturbed in the absence of a reinjection device. The reinjection box thus contributes to improving the distribution homogeneity of the fluid stream.

Without departing from the scope of the invention, the variants described in FIGS. 2A and 2B can be applied to the separation column described in FIG. 4, for which the means intended for reinjection of the fluids in a <<badly loaded>> zone is detailed in FIG. 5. The dimensions and geometry data given before remain valid.

Without departing from the scope of the invention, it is possible to apply one of the embodiments of the diverted fluid injection circuit detailed in FIGS. 1 or 2A, 2B to a column used for simulated moving bed separation comprising a central tube provided, on certain sections or parts, with several ports allowing passage of the secondary fluids and replacing the annular type distribution ring.

Figure 7A:
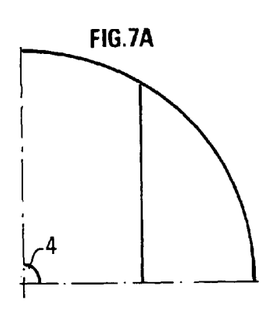
Figure 7B:
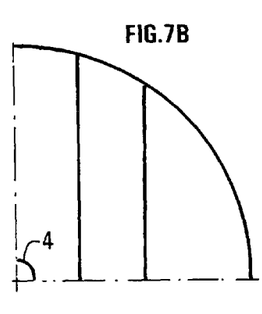
Figure 7C:
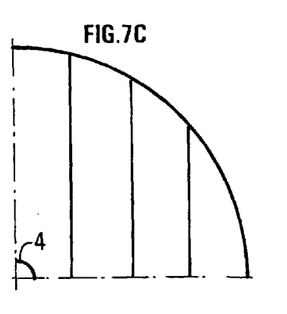

FIGS. 7A, 7B, 7C diagrammatically show several variants where plate Pi consists of several panels having a tangential or parallel type cutout.

In this case, the fluid distribution spider divides, for the instances given by way of non limitative example in FIGS. 7A, 7B and 7C, so as to supply 8, 12 or 16 plates according to variants illustrated for example in U.S. Pat. No. 5,792,346 or in patent applications FR-98/10,998 or FR-98/10,996, considering the distribution system connected to a single room.

When the column comprises a non-perforated central tube, the latter serves for example as a support for the diverted fluid reinjection device. The device can have different geometries, some of which are given by way of non limitative example in FIGS. 8, 9 and 10.

Figure 8:
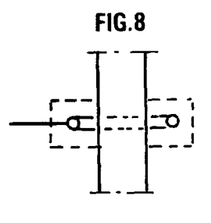
Figure 9:
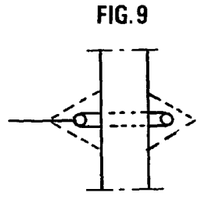
Figure 10:
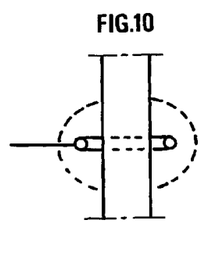

In these different embodiment variants, the walls delimiting this chamber consist of a grid that allows passage and redistribution of the diverted fluid and prevents the adsorbent bed particles from entering the reinjection means.

The geometry and the dimensions of these variants are in this case defined so as to distribute the diverted fluid as homogeneously as possible and to obtain even distribution over all of the various tangentially cut out panels.

Figure 11:
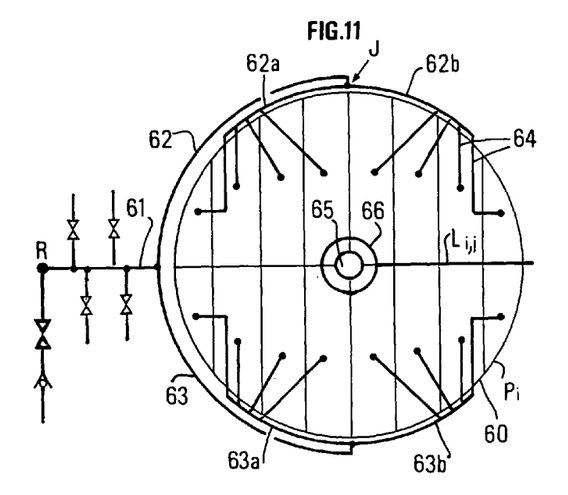
FIG. 11 is a top view of a distribution system arranged around a separation column.

FIG. 11 is a top view of a distribution system arranged on the periphery of a separation column 60. The column comprises several plates Pi whose arrangement is substantially similar to that described in the previous figures. Each plate Pi consists of several panels comprising each a single distribution-extraction-mixing chamber Ci. A plate Pi can be divided into several areas, for example 4 areas in this example. Each chamber Ci is connected to the fluid distribution and extraction system by means of transfer lines 61 arranged for example as described hereafter.

The distribution system comprises a transfer line 61 subdivided into two lines 62, 63. Lines 62 and 63 themselves are subdivided into two secondary lines 62a, 62b and 63a, 63b allowing distribution and/or extraction of the fluids to or from the four areas of the plate.

The end of a secondary line 62a, 62b, 63a, 63b, distinct from junction point J, comprises, in a given area, one or more lines 64 whose number is equal to the number of panels forming an area.

Bypass line Li,j opens into a circular ring arranged around non-perforated central tube 65 placed inside an annular reinjection chamber or annular box 66 whose geometric characteristics and dimensions are those given above in FIGS. 8, 9, 10.

Figure 12A:
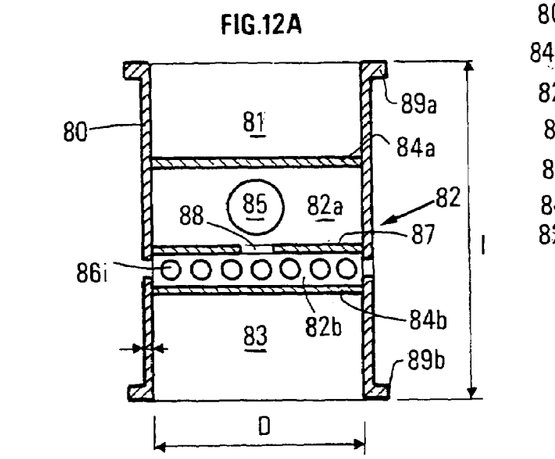
FIGS. 12A, 12B, 13 and 14 show an example of a central girder having a fluid distribution function, FIGS. 15 to 17 describe other variants suited for panels exhibiting a tangential type cutout, the column comprising no central girder.
Figure 12B:
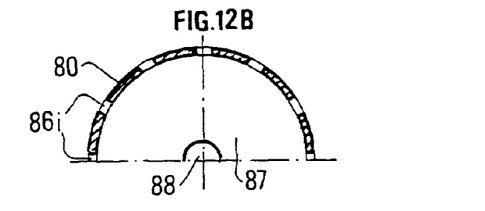

FIGS. 12A and 12B diagrammatically show an element of a perforated central mast used in the separation column as described in FIGS. 1 and 2. This element comprises a tube 80 or a substantially cylindrical tube portion having a wall thickness e, a length l and an inside diameter D.

The mast element consists for example of three parts, an upper part 81, an intermediate part 82 referred to as <<fluid distributor-collector>>, comprising several means allowing passage of one or more fluids, and a lower part 83. Parts 81 and 82 are separated by an upper sealing element 84a and parts 82 and 83 by a lower sealing element 84b so that the fluids circulate in part 82 only. In some cases, a minor fluid fraction can possibly be present in parts 81 or 83 for pressurization of the mast element for example.

The distributor-collector element is provided with various means allowing passage or circulation of fluids in the cylindrical section towards the outside and vice versa. These means are for example: a port 85 having a diameter $\Phi_5$, several ports 86i having a diameter $\Phi_6$, distributed on the periphery of the mast element. A separation element 87 such as a plate, for example provided with a central port 88, thus delimits two annular spaces 82a and 82b inside the distributor-collector element. Upper space 82a communicates with port 85 and lower space 82b with ports 86i.

If we consider a fluid distribution from the central element of the girder, the fluid(s) to be distributed flow through port 85 towards the inside of the mast element, then through port 88 of perforated plate 87 prior to being distributed to the outside of the mast through ports 86i.

Without departing from the scope of the invention, it is also possible to reverse the functions of ports 85 and 86i, the fluid flowing first through ports 86i, then through port 85.

Mast element 80 is provided, in its lower part and in its upper part, with flanges 89a and 89b respectively, or with any other means allowing notably connection between various elements so as to form a mast used as a central girder.

The elements can also be connected together by welding.

Separation element 87 can be a perforated plate or a grid.

The diameter of central port 88 is selected so as to obtain sufficient turbulence of the fluid(s) in spaces 82a and 82b to provide homogeneous distribution of the fluids through ports 86i and 85.

Port 88 is preferably located at the centre of plate 87 so that the fluid delivered through port 85 reaches the majority of ports 86i at the same time.

When separation element 87 consists of a perforated plate comprising several ports, the sum of the flow surface area of the ports is considered to provide the most homogeneous distribution possible.

In some variants, parts 81 and 83 are pressurized so as to obtain substantially the same pressures at 81, 82, 83 and to prevent any mechanical breakage of the sealing elements.

Flanges 89a and 89b and the thickness of the mast are designed to provide a sufficient stiffness in relation to the load undergone by the column.

Mast element 80 and ports 85 and 86i can have various shapes or geometries.

Figure 14:
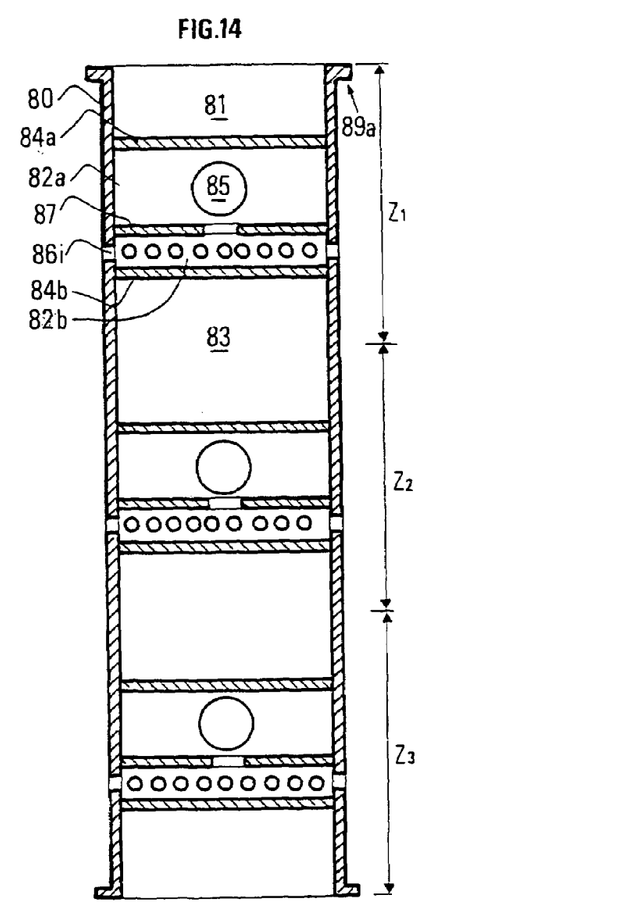

FIG. 14 shows an example of a mast element comprising, distributed over its length, three zones $Z_1$, $Z_2$ and $Z_3$ comprising each a structure similar to that given in FIG. 12A.

The structure of each zone $Z_1$, $Z_2$ and $Z_3$ is comparable, as regards the elements that constitute it, to a mast element comprising sealing means 84a, 84b confining the fluid mainly in distribution-collection part 82.

They also comprise one or more ports 85, openings 86i and a separation plate 87 as described above.

Figure 13:
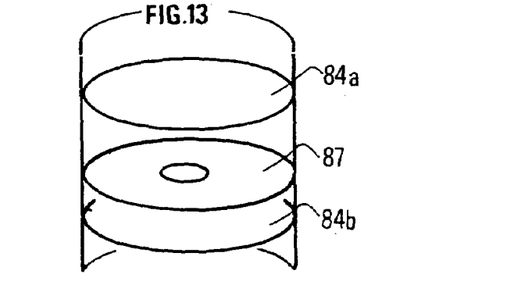

The stages for manufacturing such an element are for example as follows:

a substantially cylindrical hollow central tube is used, ports 85 and 86i are drilled according to previously determined distances and geometries, the following various elements are associated outside (FIG. 13):

a lower sealing element 84b, then, just above, a separation plate 87, then another sealing element 84a, spaced out so as to obtain a structure similar to the inside of the mast element described in FIG. 12A. This operation is started again by arranging the same elements from a given distance d between the lower sealing element of zone $Z_2$ and the upper sealing element of zone $Z_3$ for example, the assembly thus obtained is fed into the hollow tube and held up by means known to the man skilled in the art. Sealing between the plates and the hollow tube can be provided by welding or by any other means.

Figure 15:
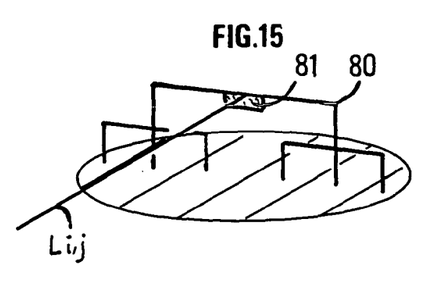
Figure 16:
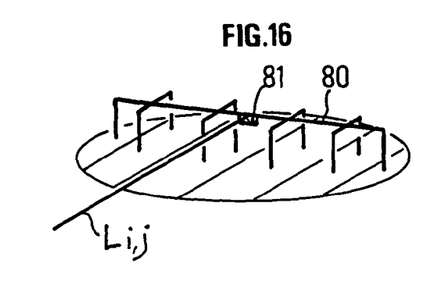
Figure 17:
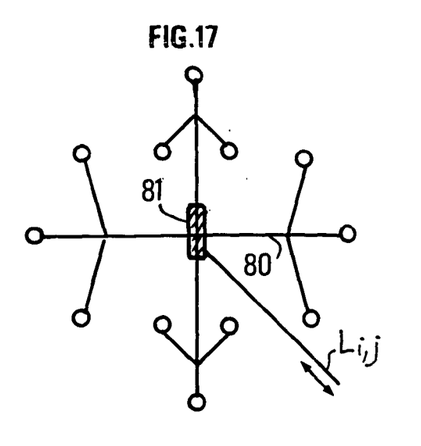

Other embodiment variants shown in FIGS. 15 to 17 are suited for cases where the separation column comprises no central tube.

These cases are particularly well-suited for small-diameter separation columns. Plates Pi consist of tangentially cut out panels, typically 3 to 5.

In the example illustrated by FIG. 15, the annular reinjection device or chamber is laid out as follows: bypass line Li,j is for example ended by a T-connected distribution ramp 80 arranged in a filtering perforated pipe 81 preferably on the principal axis of the column. Line Li,j and/or the perforated pipe is for example secured to the central branch of the distribution spider if the connection lines are arranged in a vertical plane.

FIGS. 16 and 17 diagrammatically show two other variants.

Figure 18:
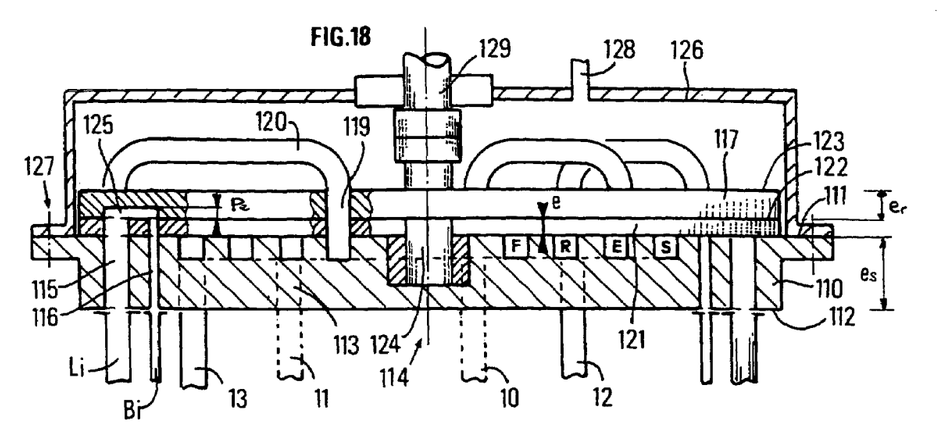
FIGS. 18, 19 and 20 show a variant of a rotary valve used in the example illustrated in FIGS. 2A and 2B.
Figure 19:
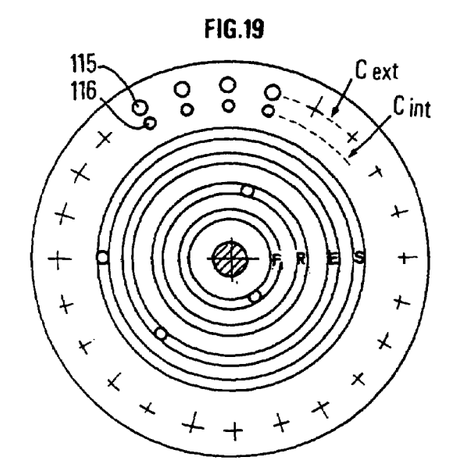
Figure 20:
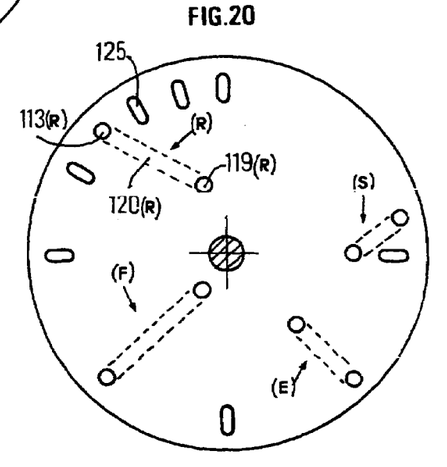

FIGS. 18, 19 and 20 illustrate the valve according to the invention and an example of positioning of the communication means allowing to carry out a stage of the process.

The fluids involved in the process circulate through lines that can be classified in three groups defined according to their function for example. Connection between the various groups is for example achieved according to a predetermined sequence.

In a separation process using four process fluids such as feed F, extract E, raffinate R and desorbent S, the various groups can be specified as follows:

GROUP 1, $G_1$,=the lines allowing transfer of the fluids referred to as process fluids, such as the extract, the raffinate, the feed, the desorbent, GROUP 2, $G_2$, =the lines allowing communication between the various ports of the rotary valve, GROUP 3, $G_3$,=the lines allowing communication of a process fluid with a bed of a separation column or between two beds (diverted fluid).

The notion of group defined for the lines can be extended to the fluids involved.

FIGS. 18 and 19 correspond to a cross-sectional view of the valve and to a top view of the stator.

The rotary valve comprises:

A stator 110 comprising:

a part of thickness <<es>>, delimited by an upper face 111 (resting face) and a lower face 112.

Four substantially concentric grooves F, R, E, S are arranged on upper face 111 from the centre of the stator. Each groove is intended for passage of a process fluid, and distribution can be performed according to an order F, R, E, S or to any other order. Each groove is connected to a line 113 running through the thickness of the stator and allowing passage for example of the process fluids coming from lines 10, 11, 12, 13.

In the description, grooves F, R, E, S belong to group $G_1$ defined above.

There are various possibilities for circulating the fluids in the grooves. In FIGS. 18 and 19, the example shows a fluid distribution performed from the most polluting to the least polluting, from centre 114 to the periphery of the valve stator.

Several Ports:

ports 115, each one being connected to a transfer line Li and to a flow surface $S_1$, are distributed for example on a circle $C_{ext}$ (FIG. 19) arranged on the periphery of the stator. The number of these ports 115 is equal to the number of transfer lines Li, ports 116, each one being connected to a bypass line (Bi) and to a flow section $S_2$, are arranged on a circle $C_{int}$ (FIG. 19) situated between the circle which is the most exterior to the stator and the first groove of the group (in this example, groove F). A port 116 corresponds to a port 115.

Flow sections $S_1$ and $S_2$ of ports 115 and 116 are determined according to the flow rate of the secondary fluids (or process fluids) and to the flow rate of the diverted fluid. The pressure drop being imposed by the granular medium for a given flow rate, the diameter of the bypass line is selected so as to have a synchronism of the flow rates of the main fluid and of the diverted fluid. Typically, the value of the $S_1/S_2$ ratio is of the order of 4, and it can range between 2 and 10.

A rotor 117 comprising:

an element of thickness <<er>> delimited by a lower face 122 and an upper face 123. The element is mounted on a shaft comprising two parts 124 and 129 coupled together.

Part 124 is secured to the stator by bearings. Part 129 runs through a bell 126, sealing being provided by systems known to the man skilled in the art.

several ports 119 running through the thickness of the rotor. These ports 119 are arranged so as to allow communication of a groove (R, F, S, E) with a process fluid transfer line (10, 11, 12, 13), means 120 such as U-shaped lines allowing communication of a port 119 with a port 115 of the stator. In this application case, there are four lines 120, a joint or liner 121 of thickness e, arranged on lower face 122 of the rotor, provides sealing between the four grooves, the various ports 115, 116, 113, means 125 for communicating a transfer line Li with a bypass line Bi, distributed on upper face 123. These means can consist of elliptical slots for example, whose major axes are for example oriented radially to the rotor.

Slots 125 arranged for example in the liner have the following characteristics:

a depth <<Pe>>, a principal axis having a sufficient length to allow communication between two ports 115 and 116 situated on the same radius of the stator in order to achieve diversion of the fluid. The length of this axis is at least equal to the distance <<d>> between the two circles $C_{int}$ and $C_{ext}$.

The value of depth <<P>> is for example greater than the value of thickness <<e>> of liner 121, slot 125 being bored at least partly in the liner arranged on lower face 122 of the rotor.

A Bell 126

Bell 126 is fastened to the stator by means 127 known to the man skilled in the art, such as screws, bolts or any other means allowing a mechanical link. A line 128 allows to deliver a fluid under pressure. Before the rotor starts rotating, the pressure in the bell is lowered so as to decrease the force exerted between the rotor and the stator and to facilitate the relative displacement between these two parts.

FIG. 19 shows the upper face of the stator, notably the following elements: ports 115 and 116 arranged in two circles, $C_{ext}$ and $C_{int}$ respectively, grooves F, R, E, S and ports 113 opening into the grooves.

FIG. 20 illustrates an example of communication of the various elements of the valve during a stage of the process. The position of the slots and of means 120 on the lower face of the rotor is shown when the four process fluids pass through four beds while the diverted fluid passes through the other twenty beds.

Slots 125 allow passage of the diverted fluid between two consecutive beds for example.

The four U-shaped lines 120 communicate a port of a groove with an external line allowing delivery or extraction of a process fluid.

Thus, in FIG. 20:

the raffinate is extracted from bed 4 by passing through a port 119 (R), a line 120 (R), a port 113 (R) and line 13, the feed is injected into bed 10, through line 10, a port 113 (F), a line 120 (F), a port 119 (F), the extract is drawn off from bed 16 through a port 119 (E), a line 120 (E), a port 113 (E) and line 12, the solvent or desorbent is introduced into bed 20 through line 11, a port 113 (S), a line 120 (S), a port 119 (S).

Suffixes R, F, S and E respectively designate the raffinate, the feed, the desorbent and the extract.

The other beds receive the diverted fluid, which corresponds to communicating a port 115 with a port 116 by means of a slot 125.

Without departing from the scope of the invention, it is possible to also provide an elliptical slot in the liner at the points where the secondary fluids are injected or drawn off. In this case, the fluids are partly injected and drawn off through the bypass line, but the four beds following injection or draw off do not undergo the internal flow rate disturbance due to the diverted fluid stream interruption.

The invention claimed is:

1. A device for separating at least one compound from a mixture by adsorption with a simulated moving bed, comprising at least:
   an enclosure or column comprising adsorbent beds (Ai), at least two adsorbent beds being separated by at least one fluid distribution and extraction plate (Pi), the plate comprising one or more panels allowing distribution, mixing and/or extraction of fluids, each panel comprising a single distribution, mixing and/or extraction chamber (Ci),
   a plurality of lines (10, 11, 12, 13, Ti) for extraction or injection of secondary fluids,
   a bypass circuit communicating a distribution plate with at least one bypass line (Li,j), wherein the device comprises means (14, Voi,j, 20) for communicating said at least one single distribution, mixing and/or extraction chamber (Ci) with at least one bypass line (Li,j),
   at least one end of said at least one bypass line communicates with a zone (Ri, R'i) of an adsorbent bed, said zone being distinct from any distribution chamber, and another end of said at least one bypass line is connected to chamber (Ci).

2. A device as claimed in claim 1, wherein said means for communicating ($C_1$) with (Li,j) comprises at least one valve (Voi,j) arranged on at least one bypass line (Li,j) and in that an end of the bypass line that is not connected to the zone of the adsorbent bed is connected to a delivery and/or extraction line (Ti), which line (Ti) is connected to chamber (Ci).

3. A device as claimed in claim 1, wherein said means for communicating (Ci) with (Li,j) comprises at least one rotary valve (20), said rotary valve being connected to at least one delivery and/or extraction line (Ti) and to at least one bypass line (Li,j), said valve comprising means allowing at least to communicate a delivery and/or extraction line with at least one bypass line.

4. A device as claimed in claim 3, wherein said rotary valve (20) is in communication with a plurality of groups of lines, group $G_1$, group $G_2$ and group $G_3$, said valve comprising:
   a stator (110) provided with several means (E, F, R, S) for circulation of a fluid(s) of a group $G_1$, means (115, 116) allowing passage of at least two fluids $F_1$, $F_2$ belonging to group $G_3$, said means (115, 116) comprising a substantially equal number of passages, means (115) having a flow section $S_1$, means (116), having a flow section $S_2$, different from $S_1$,
   a rotor (117) equipped with means (119) for passage of fluids of a group $G_3$ and means (120) for communication of either the fluids of group $G_1$ with group $G_3$, or of group $G_3$ with group $G_3$, and
   means (122) for communicating at least two fluids of group $G_3$.

5. A device as claimed in claim 4, wherein the means for passage of fluid $F_1$ and of fluid $F_2$ have flow sections $S_1$ and $S_2$ respectively, wherein $S_1/S_2$ ratio is 2 to 10.

6. A device according to claim 5, wherein the $S_1/S_2$ ratio is about 4.

7. A device as claimed in claim 4, said means communication of fluids of group $G_3$ consists of slots (122) provided in a layer of material or liner deposited on the lower face of the rotor.

8. A device as claimed in claim 7, wherein a slot (122) has a depth at least equal to the thickness of the liner.

9. A device as claimed in claim 7, wherein said circulation means (E, R, S, F) comprises a plurality of grooves arranged on an upper face of the stator and slots (122) are provided in the liner.

10. A device as claimed in claim 4, wherein circulation means (E, R, S, F) are 4 in number.

11. A device as claimed in claim 1, wherein said enclosure comprises a non-perforated central tube over at least part of the length thereof, and the panels forming a plate comprise a tangential cutout; and wherein zone (Ri, R'i) comprises at least one diverted fluid distribution means (53, 54), and the end of bypass line (Li,j) connected to chamber (Ci) opens into said diverted fluid distribution means (53, 54).

12. A device as claimed in claim 11, wherein a fluid distribution circuit is arranged around said enclosure and comprises a main line (61) divided into a plurality of secondary lines (62, 63, 62a, 62b) so that the fluid(s) reach the panels forming a plate substantially at the same time.

13. A device as claimed in claim 11, wherein the plates form a parallel cutout and in that the fluid distribution circuit comprises a main line, and a bypass line connected to an adsorbent bed by means of a device comprising transfer ports.

14. A device as claimed in claim 11, wherein said perforated means comprises a wall (55) forming an angle α with the central tube and in that said ring (53) is located at a distance a from said grid.

15. A device as claimed in claim 1, wherein a plate is delimited by a lower grid (6) and an upper grid (7) and in that an end of the bypass line connected to the adsorbent bed is connected to a distribution means (30) arranged above said upper grid.

16. A device as claimed in claim 1, wherein a plate comprises a plurality of panels forming a radial cutout, the enclosure comprises a central tube and a secondary fluid distribution ring in communication with a distribution plate, and a diverted fluid distribution means, said means being arranged below the distribution ring and said means being connected to the end of the bypass line, said bypass line being connected to a zone of an adsorbent bed.

17. A device as claimed in claim 16, wherein said diverted fluid distribution means comprise at least one diverted fluid distribution ring (53), said ring (53) being arranged in a perforated means (55), said means having a substantially conical shape.

18. A device as claimed in claim 1, wherein said column comprises a substantially central mast comprising one or more mast elements (80), including at least:
   an upper part (81),
   A distibutor-collector part (82) comprising one or more secondary ports (86i) and at least one main port (85), the flow sections of ports (85) and (86i) being different,
   a lower part (83)
   a distibutor-collector part(s) (82) are arranged between an upper part (81) and a lower part (83)

a sealing element (84*a*) arranged between distributor-collector part (82) and lower part (83), a separation element (87) arranged on distributor-collector part (82), thus delimiting two fluid circulation spaces (82*a*, 82*b*).

19. A device according to claim 1, comprising at least one bypass line Li,j with j=i+1, in which a fluid is diverted from a chamber (Ci) to a zone (Ri+1).

20. In a process comprising injection of a diverted fluid in a simulated moving bed separation process, comprising at least the following stages:

circulating a main fluid through a plurality of adsorbent beds in an enclosure, at least two adsorbent beds being separated by at least one fluid distribution and extraction plate (Pi), the plate comprising one or more panels allowing distribution, mixing and/or extraction of fluids, said panels each comprising a single distribution, mixing and/or extraction chamber     injecting and extracting secondary fluids comprising feed, desorbent, extract and raffinate according to a sequential order to achieve separation of the constituents of the feed,     injecting a diverted fluid, the improvement wherein at least part of the main fluid is circulated outside the enclosure allowing separation by means of a bypass line comprising at least two ends, one end being connected to a zone of an adsorbent bed distinct from distribution chambers so as to inject and to extract part of the main fluid in the zone, and another end of said bypass line being connected to chamber (Ci).

21. A process as claimed in claim 20, wherein a fraction of the main fluid is drawn off from a zone of an adsorbent bed Ai and said fraction is injected into a chamber Ci.

22. A process as claimed in claim 20, wherein paraxylene is separated from aromatic hydrocarbon-containing feeds with eight carbon atoms.

23. A process as claimed in claim 20, wherein a fraction of the main fluid is drawn off from a chamber (Ci) corresponding to a plate Pi and the main fluid fraction drawn off is injected into a zone of adsorbent bed Ai+1.

24. A device for separating at least one compound from a mixture by adsorption with a simulated moving bed, comprising at least:

an enclosure or column comprising adsorbent beds (Ai), at least two adsorbent beds being separated by at least one fluid distribution and extraction plate (Pi), the plate comprising one or more panels allowing distribution, mixing and/or extraction of fluids, each panel comprising a single distribution, mixing and/or extraction chamber (Ci),     a plurality of lines (10, 11, 12, 13, Ti) for extraction or injection of secondary fluids,     a bypass circuit communicating a distribution plate with at least one bypass line (Li,j), wherein     the device comprises means (14, Voi,j, 20) for communicating said at least one single distribution, mixing and/or extraction chamber (Ci) with at least one bypass line (Li,j),     at least one end of said at least one bypass line communicates with a zone (Ri, R'i) of an adsorbent bed, said zone being distinct from any distribution chamber, and another end of said at least one bypass line is connected to chamber (Ci).

\* \* \* \* \*